(12) United States Patent
Sharratt et al.

(10) Patent No.: US 8,742,181 B2
(45) Date of Patent: *Jun. 3, 2014

(54) PROCESS FOR ISOMERIZING A (HYDRO)FLUOROALKENE

(71) Applicants: Andrew Paul Sharratt, Cheshire (GB); John Charles McCarthy, Cheshire (GB)

(72) Inventors: Andrew Paul Sharratt, Cheshire (GB); John Charles McCarthy, Cheshire (GB)

(73) Assignee: Mexichem Amanco Holding S.A. de C.V., Tlalnepantla (MX)

( * ) Notice: Subject to any disclaimer, the term of this patent is extended or adjusted under 35 U.S.C. 154(b) by 0 days.

This patent is subject to a terminal disclaimer.

(21) Appl. No.: 13/683,893

(22) Filed: Nov. 21, 2012

(65) Prior Publication Data

US 2013/0079562 A1 Mar. 28, 2013

Related U.S. Application Data

(63) Continuation of application No. 12/450,748, filed as application No. PCT/GB2008/001282 on Apr. 11, 2008, now Pat. No. 8,410,324.

(30) Foreign Application Priority Data

Apr. 11, 2007 (GB) .................................. 0706978.4

(51) Int. Cl.
  *C07C 21/00* (2006.01)
(52) U.S. Cl.
  USPC .......................................... 570/153; 570/151
(58) Field of Classification Search
  None
  See application file for complete search history.

(56) References Cited

U.S. PATENT DOCUMENTS

| | | | |
|---|---|---|---|
| 2,700,686 A | 1/1955 | Dickey et al. | |
| 2,889,379 A | 6/1959 | Ruh et al. | |
| 2,918,501 A | 12/1959 | Brehm et al. | |
| 2,931,840 A | 4/1960 | Marquis | |
| 2,996,555 A | 8/1961 | Rausch | |
| 3,000,979 A | 9/1961 | Gibbs et al. | |
| 3,398,204 A | 8/1968 | Gallant | |
| 3,674,665 A | 7/1972 | Cristol et al. | |
| 3,739,036 A | 6/1973 | Valicenti et al. | |
| 3,793,229 A | 2/1974 | Groppelli et ai. | |
| 4,093,670 A | 6/1978 | Ozawa et al. | |
| 4,220,608 A | 9/1980 | Feiring | |
| 4,465,786 A | 8/1984 | Zimmer et al. | |
| 4,798,818 A | 1/1989 | Baizer et al. | |
| 5,672,803 A | 9/1997 | Smith et al. | |
| 5,679,875 A | 10/1997 | Aoyama et al. | |
| 5,763,711 A | 6/1998 | Ito | |
| 5,811,603 A | 9/1998 | Elsheikh | |
| 5,986,151 A | 11/1999 | Van Der Puy | |
| 6,111,150 A | 8/2000 | Sakyu et al. | |
| 6,329,559 B1 | 12/2001 | Sievert et al. | |
| 6,734,332 B1 | 5/2004 | Slaugh et al. | |
| 7,435,700 B2 * | 10/2008 | Amos et al. | 502/100 |
| 7,709,691 B2 | 5/2010 | Wang et al. | |
| 8,044,252 B2 | 10/2011 | Nappa et al. | |
| 2005/0038302 A1 | 2/2005 | Hedrick et al. | |
| 2006/0122441 A1 | 6/2006 | Tung | |
| 2006/0269484 A1 | 11/2006 | Knopeck et al. | |
| 2007/0004585 A1 | 1/2007 | Amos et al. | |
| 2007/0112230 A1 | 5/2007 | Mukhopadhyay et al. | |
| 2007/0129579 A1 | 6/2007 | Wang et al. | |
| 2007/0197842 A1 | 8/2007 | Mukhopadhyay et al. | |
| 2008/0051611 A1 | 2/2008 | Wang et al. | |
| 2008/0103342 A1 * | 5/2008 | Wang et al. | 570/256 |
| 2009/0099395 A1 | 4/2009 | Sakyu et al. | |
| 2009/0209792 A1 * | 8/2009 | Sharratt et al. | 570/165 |

FOREIGN PATENT DOCUMENTS

| | | |
|---|---|---|
| DE | 1140928 | 12/1962 |
| DE | 2128341 | 12/1971 |
| EP | 0097571 | 1/1984 |
| EP | 0169711 | 1/1986 |
| EP | 0270006 | 11/1987 |
| EP | 0366797 | 1/1989 |
| EP | 0461297 | 7/1990 |
| EP | 0436989 | 12/1990 |
| EP | 0502605 | 1/1992 |
| EP | 486333 | 5/1992 |
| EP | A502605 | 10/1992 |
| EP | 0644173 | 5/1993 |
| EP | 0752403 | 7/1996 |
| EP | 0726243 | 8/1996 |
| EP | 0773061 | 5/1997 |
| EP | 0939071 | 9/1999 |
| EP | 0957074 | 11/1999 |
| EP | 0974571 | 1/2000 |
| EP | 1067106 | 1/2001 |
| EP | 1350564 | 10/2003 |
| EP | 1502906 | 3/2005 |
| EP | 1900716 | 8/2007 |
| EP | 1918269 | 10/2007 |

(Continued)

OTHER PUBLICATIONS

Office Action issued by China Patent Office in 200880016249.4, dated Sep. 13, 2012.

(Continued)

*Primary Examiner* — Sudhakar Katakam
(74) *Attorney, Agent, or Firm* — Ryan Kromholz & Manion, S.C.

(57) ABSTRACT

A process for isomerizing a (hydrohalo)fluoroalkene, the process comprising contacting the (hydrohalo)fluoroalkene with a catalyst a catalyst which is a chromia-containing catalyst supported on $AlF_3$ or fluorinated alumina.

11 Claims, No Drawings

(56) References Cited

FOREIGN PATENT DOCUMENTS

| | | |
|---|---|---|
| EP | 2338866 | 6/2011 |
| FR | 2342952 | 9/1977 |
| GB | 1407696 | 9/1975 |
| JP | 55130926 | 10/1980 |
| JP | 11-140002 | 5/1999 |
| JP | 2005536424 | 12/2005 |
| JP | 2006503961 | 2/2006 |
| SU | 507551 | 3/1976 |
| WO | WO 93/04025 | 3/1993 |
| WO | WO92/32935 | 12/1995 |
| WO | WO96/11896 | 4/1996 |
| WO | WO 97/05089 | 2/1997 |
| WO | WO98/10862 | 3/1998 |
| WO | WO 98/37043 | 8/1998 |
| WO | WO 99/62857 | 12/1999 |
| WO | WO 2004/018095 | 3/2004 |
| WO | WO 2005/012212 | 2/2005 |
| WO | WO 2005/023984 | 3/2005 |
| WO | WO2005/037431 | 4/2005 |
| WO | WO 2005/037743 | 4/2005 |
| WO | WO 2005/042451 | 5/2005 |
| WO | WO2005/105947 | 11/2005 |
| WO | WO 2005/108332 | 11/2005 |
| WO | WO 2005/108333 | 11/2005 |
| WO | WO 2005/108334 | 11/2005 |
| WO | WO 2006/106353 | 10/2006 |
| WO | WO2008/106533 | 10/2006 |
| WO | WO 2007/056194 | 5/2007 |
| WO | WO 2007/079431 | 7/2007 |
| WO | WO 2007/145171 | 12/2007 |
| WO | WO 2008/002500 | 1/2008 |
| WO | WO2008/008351 | 1/2008 |
| WO | WO 2008/030440 | 3/2008 |
| WO | WO2008/030443 | 3/2008 |
| WO | WO 2008/040949 | 4/2008 |
| WO | WO 2008/040969 | 4/2008 |
| WO | WO 2008/054781 | 5/2008 |
| WO | WO 2008/054782 | 5/2008 |
| WO | WO 2008/075017 | 6/2008 |
| WO | WO 2009/140563 | 11/2009 |

OTHER PUBLICATIONS

Office Action from Chinese State intellectual Property Office dated Dec. 27, 2012 regarding application No. 200880016249.4, 8 pages.
International Search Report dated Oct. 21, 2008 from PCT/GB2008/001282.
Burton et al., "Prep of E-1,2,3,3,3-pentafluopropene, . . . pentafluopropene", J of Fluorine Chemistry, Elsevier, NL, vol. 44, No. 1, Jul. 1, 1989, pp. 167-174.
Sianesi et al., Ann. Chim. (Rome), 55(8-9), pg. 850-861, 1965 (+Eng. Trans).
Buchner et al., Chemistry: A European Journal, vol. 4, p. 1799-1809, 1998.
Joyce et al., J. Am. Chem. Soc., 70, p. 2529-2532, 1948.
Haszeldine at al., J. Chem. Soc. Perkin Trans. 1, 1979, p. 1943-1947.
Haszeldine at al., J. Chem. Soc., 1970, p. 414-421.
Haszeldine et al., J. Chem. Soc. Perkin Trans. 1, 1974, p. 1303-1307.
Haszeldine at al., J. Chem. Soc. Perkin Trans. 1, 1976, p. 2349-2353.
Haszeldine at al., J. Chem. Soc., 1953, p. 3371-3378.
Meyer et al., Synthesis, 2000, 10, p. 1479-1490.
Atherton et al., J. Chem. Soc., 1971, p. 366-371.
Boche et al., J. Chem. Ber., 1981, p. 4005-4009, English Abstract.
Baklouti et al., J. Fluor. Chem., 1981, p. 181-190, English Abstract.
Banks et al., J. Fluor. Chem., 1997, 82, p. 171-174.
European Patent Office Official Action dated Feb. 18, 2013 regarding European Pat. Appln. Serial No. 08736947.6, 5 pages.
Japanese Patent Office Official Action dated Apr. 23, 2013 regarding Japanese Pat. Appln. Serial No. 2010-502571, 2 pages. No English translation available.
Smith M.B.; March, J., Advanced Organic Chemistry, 5th edition, 2001, p. 1195.
USPTO Office Action regarding U.S. Appl. No. 12/450,748 dated Feb. 10, 2012, 7 pages.

\* cited by examiner

PROCESS FOR ISOMERIZING A (HYDRO)FLUOROALKENE

RELATED APPLICATIONS

This application is a Continuation of co-pending U.S. patent application Ser. No. 12/450,748 filed 8 Mar. 2010, which is the U.S. National Phase of International Patent Application Serial No. PCT/GB2008/001282.

BACKGROUND OF THE INVENTION

The subject invention relates to a process for isomerising alkenes, particularly (hydrohalo)-fluoroalkenes. Many alkenes, including (hydrohalo)fluoroalkenes, can exist in two isomeric forms depending on the arrangement of the substituents around the double bond. This isomerism is called geometric, cis/trans or E/Z isomerism. In the E/Z notation, Z (zusammen) means together and corresponds to the term cis and E (entgegen) means opposite and corresponds to the term trans. Whether a molecular configuration is designated E or Z is determined by the Cahn Ingold Prelog priority rules. For each of the two atoms in the double bond, it is necessary to individually determine which of the two substituents is of a higher priority. If both of the substituents of higher priority are on the same side, the arrangement is Z; if they are on opposite sides the arrangement is E.

Corresponding E and Z isomers typically have differing physical (e.g. boiling point) and/or chemical properties (e.g. reactivity). These differing properties may be attributed to the fact that the dipole moment of the substituents will tend to add for a cis or Z isomer, while for a trans or E isomer, the dipoles of the substituents will tend to cancel each other out. As a result of the differing physical and/or chemical properties of E/Z isomers, one of the isomers may be preferred over the other for a particular application.

Thus, it may be desirable to be able to convert one E/Z isomer to the other.

In typical processes for preparing alkenes such as (hydrohalo)fluoroalkenes, both of the E/Z isomers will typically be formed. The amount of each E/Z isomer formed may depend on a number of factors, such as the kinetic and thermodynamic stability of each E/Z isomer. If, as explained above, one isomer is preferred over the other then depending on the utility of the (hydrohalo)fluoroalkenes, it may then be desirable to convert one E/Z isomer to the other. Alternatively, it would be desirable during the process for preparing alkenes such as (hydrohalo)fluoroalkenes to isomerise the one E/Z isomer to the other (preferred) E/Z isomer.

It is described in WO 2008/008351 that it is possible to increase the ratio of the Z to E isomers in 1,2,3,3,3 pentafluoropropene. This is said to be possible using a catalyst supported on $AlF_3$ or carbon, which catalyst is selected from $SbCl_wF_{5-w}$, $TiCl_xF_{4-x}$, $SnCl_yF_{4-y}$ and $TaCl_zF_{5-z}$, wherein w is from 0 to 4, x is from 0 to 3, y is from 0 to 3 and z is from 0 to 4. Further, in the Examples of WO 2008/030443 there is described the partial isomerisation of E R-1234ze (1,3,3,3-tetrafluoropropene) to Z R-1234ze over a crushed chromium oxide gel pellet catalyst.

The subject invention addresses the deficiencies and problems outlined above in a first aspect by providing a process for isomerising a (hydrohalo)fluoroalkene by contacting the (hydrohalo)fluoroalkene with a specific catalyst. Also provided is the use of the catalyst for isomerising a (hydrohalo)fluoroalkene.

In a further aspect, there is provided a process for isomerising a (hydrohalo)fluoroalkene, the process comprising (i) contacting a E-(hydrohalo)fluoroalkene with a catalyst to convert the E-(hydrohalo)fluoroalkene to the Z-(hydrohalo)fluoroalkene. Conveniently, the Z-(hydrohalo)fluoroalkene can be recovered, and e.g. used in a subsequent procedure.

In a further aspect, the subject invention provides the use of a catalyst for isomerising a (hydrohalo)fluoroalkene, the use comprising (i) contacting a E-(hydrohalo)fluoroalkene with a catalyst to convert the E-(hydrohalo)fluoroalkene to the Z-(hydrohalo)fluoroalkene. Conveniently, the Z-(hydrohalo)fluoroalkene can be recovered, and e.g. used in a subsequent procedure.

By "isomerisation" in this context is preferably meant changing the ratio of the E and Z isomers (e.g. increasing the level of Z isomer) from what it was previously or, in a situation where the isomerisation is carried out in situ, for instance as part of a preparation step for the (hydrohalo)fluoroalkene, changing the ratio of E and Z isomers (e.g. increasing the level of Z isomer) compared to what it would have been if the catalyst had not been utilised.

In envisaged embodiments, the invention may be used as a separate process step to enhance the level of Z isomer in an E/Z blend of a given (hydrohalo)fluoroalkene. Alternatively, the catalytic process of the invention enhancing the level of the Z isomer may be incorporated as an in situ step in the synthesis, conveniently the last step of the synthesis, of the desired (hydrohalo)fluoroalkene. Such a synthesis would thereby result in an enhanced Z isomer level in the resultant (hydrohalo)fluoroalkene.

In a further aspect, the invention also provides an isomer blend produced according to a process of the invention. The invention also provides a refrigerant comprising an isomer blend produced according to the process of the invention, and an automobile having an air conditioning system utilizing such an isomer blend.

Conveniently in an aspect of the invention, the invention may work by changing the E/Z isomer ratio from that which is the kinematic equilibrium of isomers, from the reaction preparing the (hydrohalo)fluoroalkene, conveniently to enhance the level of the Z isomer.

In a further aspect of the invention, there is provided a process for making a (hydrohalo)fluoroalkene composition comprising an enhanced level of Z isomer, conveniently a level of Z isomer enhanced beyond the level present when the (hydrohalo)fluoroalkene was formed in the preparative reaction conditions, or the kinematic equilibrium level of the Z isomer of the (hydrohalo)fluoroalkene, comprising the step of using a catalyst. Conveniently this aspect of the invention may comprise a clean up step which enhances the level of Z isomer in such a composition.

In an envisaged aspect, it may be provided that the catalyst utilised is not a zinc/chromia catalyst, which may contain between 0.01% and 20% zinc, when the process is carried out in situ as part of a synthesis of a $C_{3-6}$ (hydro) fluoroalkene.

Unless otherwise stated, as used herein a "(hydrohalo)fluoroalkene" is an alkene which exists in E and Z isomers and in which at least one of the hydrogen atoms has been replaced by fluorine. When there is at least one hydrogen atom present and no halogens (other than fluorine), the (hydrohalo)fluoroalkene is denoted a hydrofluoroalkene. Optionally, at least one of the hydrogen atoms may also replaced by a halogen selected from chlorine, bromine and iodine (i.e. a hydrohalofluoroalkene or a halofluoroalkene). Put another way, a (hydrohalo)fluoropropene (for example) may be represented by the formula $CX_3CX=CX_2$ where X=H, F, Cl, Br or I, provided that at least one X is F and at least one X is H, Cl, Br, or I.

Preferably, the (hydrohalo)fluoroalkene contains from 2 to 10 carbon atoms, i.e. it is a $C_{2-10}$ (hydrohalo)fluoroalkene. The process of the invention is particularly suitable for isomerising $C_{3-7}$ (hydrohalo)fluoroalkenes, especially (hydrohalo)fluoropropenes, fluorobutenes and fluoropentenes, particularly (hydrohalo)fluoropropenes.

By way of example and for simplicity, unless otherwise stated, the remainder of the description will describe the process of the invention with reference to the isomerisation of (hydrohalo)fluoropropenes. The skilled person will however understand that such discussion is equally applicable to the isomerisation of other (hydrohalo)fluoroalkenes, for example (hydrohalo)fluoroethenes, butenes, pentenes and hexenes. Conveniently the invention is particularly applicable to hydrofluoroalkenes.

As explained above, (hydrohalo)fluoroalkenes suitable for isomerisation by the process of the invention may contain 0, 1, 2, 3, 4 or 5 halogen atoms selected from Cl, Br and I (providing that the (hydrohalo)fluoropropenes contain at least one hydrogen or halogen atom), 1, 2, 3, 4 or 5 fluorine atoms, and a balancing number of hydrogen atoms. Preferred (hydrohalo)fluoropropenes are those having from 2 to 5 fluorine atoms (and thus from 1 to 4 atoms selected from H, Cl, Br and I), particularly 4 or 5 fluorine atoms (and thus 1 or 2 atoms selected from H, Cl, Br and I). Conveniently, the (hydrohalo)fluoropropenes do not contain Cl, Br or I atoms, particularly no Br or I. Other preferred (hydrohalo)fluoroalkenes likewise have from 2 to 5 fluorine atoms, particularly 4 or 5, and may conveniently contain no Cl, Br or I, particularly no Br or I.

Accordingly, a preferred group of (hydrohalo)fluoropropenes suitable for isomerisation by the process of the invention may be represented by the formula $CX_3CX=CX_2$ wherein X=H or F, provided that from 1 to 5 of the X's=F. In other words, such preferred (hydrohalo)fluoropropenes include hydrofluoropropenes selected from mono- di-, tri-, tetra- and penta-fluoropropenes.

Thus, the preferred hydrofluoropropenes particularly suitable for isomerisation by the process of the invention are selected from the monofluoropropene 1-fluoropropene ($CH_3CH=CHF$), the difluoropropenes 1,2-difluoropropene ($HFC=CFCH_3$) and 1,3-difluoropropene ($HFC=CHCH_2F$), the trifluoropropenes 1,2,3-trifluoropropene ($HFC=CFCH_2F$) and 1,3,3-trifluoropropene ($HFC=CHCF_2H$), the tetrafluoropropenes 1,3,3,3-tetrafluoropropene ($HFC=CHCF_3$) and 1,2,3,3-tetrafluoropropene ($HFC=CFCF_2H$), and the pentafluoropropene 1,2,3,3,3-pentafluoropropene ($HFC=CFCF_3$).

A particularly preferred hydrofluoropropene for use in the process of the invention is 1,2,3,3,3-pentafluoropropene ($HFC=CFCF_3$), which is also known as HFC-1225ye. Also particularly preferred is 1,3,3,3-tetrafluoropropene ($HFC=CHCF_3$), also known as R-1234ze.

Unless otherwise stated, as used herein, a "catalyst" is any catalyst capable of facilitating the conversion of an E isomer of a (hydrohalo)fluoroalkene to a Z isomer. Such catalysts include those selected from Lewis acid catalysts, chromia and chromia-containing catalysts, alumina containing catalysts, supported liquid catalysts and mixtures thereof.

The catalyst may be present in any suitable amount in the process of the invention. Typically, the weight ratio of catalyst to (hydrohalo)fluoroalkene in the process of the invention is in the range of from 1:1000 to 10:1, such as from 1:500 to 1:1, e.g. from 1:100 to 1:10.

Unless otherwise stated, as used herein, a "Lewis acid catalyst" is any catalyst capable of accepting a pair of electrons to form a coordinate covalent bond. Suitable Lewis acid catalysts include antimony pentahalides (e.g. $SbF_5$), chromium oxides and chromium oxyfluorides, aluminium oxide, aluminium trihalides (e.g. $AlCl_3$) and aluminium oxyhalides, iron (III) halides (e.g. $FeCl_3$), boron trihalides (e.g. $BF_3$), niobium or tantalum pentahalides (e.g. $NbCl_5$, $TaCl_5$), and ytterbium(III) triflate ($Yb(CF_3SO_3)_3$).

The Lewis acid catalysts may be unsupported or supported, but are preferably unsupported. Suitable supports for Lewis acid catalysts if utilised include graphite, chromia or alumina.

Unless otherwise stated, as used herein, an "alumina containing catalyst" is any catalyst comprising aluminium or a compound of aluminium (e.g. $Al_2O_3$, fluorided alumina (AlOxFy) or $AlF_3$, including catalysts based on alumina supports.

Unless otherwise stated, as used herein, a "chromia containing catalyst" is any catalyst comprising chromium or a compound of chromium. Typically, the chromium or compound of chromium present in the catalysts of the invention is an oxide, oxyfluoride or fluoride of chromium such as chromium oxide ($Cr_2O_3$). Such catalysts may be amorphous or at least partially crystalline, or substantially crystalline.

The chromia containing catalysts may be provided in any suitable form known in the art. For example, they may be provided in the form of pellets or granules of appropriate size for use in a fixed bed or a fluidised bed. The catalysts may be supported or unsupported. If the catalyst is supported, suitable supports include $AlF_3$, fluorinated alumina or activated carbon.

The chromia containing catalysts may contain at least one additional metal. The or each additional metal may be in elemental form or a compound of the metal. Typically, the or each metal is selected from zinc, magnesium, nickel, cobalt, silver, copper, aluminium, tin, zirconium and mixtures thereof. Preferred metals are zinc, magnesium, aluminium, nickel and cobalt, especially zinc. For example, suitable zinc/chromia catalysts are described in WO 2006/106353 and WO 98/10862, the content of which is as far as they refer to zinc/chromia catalysts and their preparation are incorporated by reference. The or each metal present in the chromia catalyst is preferably present in the chromia at a level of at least 0.01%, preferably at least 0.1%, preferably at least 1%, preferably at least 3% by weight of the catalyst. Conveniently the or each metal is present at a level of no more than 20%, conveniently no more than 15%, conveniently no more than 10% by weight of the catalyst.

Suitable supported catalysts include $SbF_5$ intercalated onto graphite. A suitable example of a liquid phase catalyst is $SbF_5$ Typically, the isomerisation process is carried out at a temperature of from −50 to 400° C. The process may be carried out at sub- or super-atmospheric pressure, for example at from about 0 to about 30 bara.

Preferably, the process is conducted at a temperature of from 20 to 350° C., more preferably from 50 to 300° C. Preferably, the process is conducted at a pressure of from 5 to 20 bar. Of course, the skilled person will appreciate that the preferred conditions (e.g. temperature, pressure) for conducting the process of the invention may vary depending on factors such as the nature of the (hydrohalo)fluoroalkene being isomerised and the catalyst being employed.

The contact time of the E-(hydrohalo)fluoroalkene or E/Z mix with the catalyst may vary depending on, for example, the nature of the catalyst and/or (hydrohalo)fluoroalkene and/or the conditions use in the process of the invention, e.g. temperature and/or pressure. Typically, however, the contact time will range from about 0.1 seconds to about 100 hours, preferably from 0.5 seconds to 10 hours, for example from 1 second to 1 hour.

The preferred phase in which the (hydrohalo)fluoroalkene isomer blend and the catalyst are contacted will depend on the nature of the catalyst used, the required conditions and the nature of the specific (hydrohalo)fluoroalkene. Thus, the process could be carried out between heterogenous or homogenous phases, including supercritical phases.

An inert solvent (i.e. one that shows no interaction with the catalyst or the (hydrohalo)fluoroalkene feed) may also be used to aid contacting of phases, remove or supply heat, and so on.

Suitable inert solvents include perfluoroalkanes.

The process of the invention can be carried out in any suitable apparatus, such as a static mixer, a stirred tank reactor or a stirred vapour-liquid disengagement vessel. The process may be carried out batch-wise or continuously. Either the batch-wise process or the continuous process may be carried out in a "one-pot" fashion, or using two or more than discrete reaction zones and/or reaction vessels.

The process of the invention can be carried out in a vapour phase reactor, for which suitable process conditions and apparatus are well known in the art. To this end we refer to WO 06/106353 and WO 98/10862, the contents of which are specifically incorporated herein by reference, in particular in as far as they relate to vapour phase reactors and suitable vapour phase process conditions.

The process of the invention may conveniently be carried out in the presence of hydrogen fluoride (HF). Particularly when using a chromia-containing catalyst, it is believed that the use of HF may help to prevent coking of the catalyst. However, when using a chromia-containing catalyst, it may be desirable not to use HF in order to prevent any hydrofluorination of the (hydrohalo)fluoroalkene. The presence (and amount) of HF will depend on a number of factors such as reaction temperature and pressure and, of course, the (hydrohalo)fluoroalkene being isomerised.

If HF is present, it may be present in an amount of from 0.1 to 99.9 mol %, preferably from 20 to 80 mol %, such as from 40 to 60 mol % based on the total amount of (hydrohalo)fluoroalkene being isomerised.

By way of example and for simplicity, unless otherwise stated, the remainder of the description will describe the process of the invention with reference to the isomerisation of HFC-1225ye. The skilled person will understand that such discussion is equally applicable to the isomerisation of other (hydrohalo)fluoropropenes, or indeed other (hydrohalo)fluoroalkenes, such as (hydrohalo)fluoroethenes, butenes, pentenes and hexenes.

The structures of the Z and E isomers of HFC-1225ye are shown below.

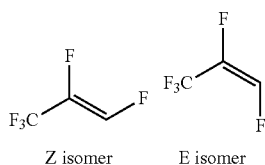

Z isomer    E isomer

The physical and chemical properties of these isomers are different. For example, the E isomer is thermodynamically less stable than the Z-isomer. Also, the boiling points of the two isomers are different. In more detail, the Z isomer has a normal boiling point of −19.9° C., and the E isomer has a normal boiling point of −15.6° C.

In processes used to prepare HFC-1225ye, a mixture of the Z and E isomers typically will be formed. If separation of the isomers is required (e.g. if one isomer is preferred over the other for a certain application) it is possible to separate the isomers using distillation. However, this is time consuming, and potentially uneconomic and wasteful if the undesired isomer is not used.

In utilities where it is preferable to increase the level of the Z isomer in the blend, it is possible using the method of the invention to increase the level of Z isomer by isomerising E isomer present in the blend to the Z isomer. The limit of how much E isomer can be converted to Z isomer is determined by thermodynamic considerations.

Alternatively, it may be preferable to carry out a process for preparing HFC-1225ye so that only the preferred isomer is substantially formed. For example, HFC-1225ye may be prepared by dehydrohalogenation, e.g. by dehydrofluorination of $CF_3CFHCF_2H$ (HFC-236ea) or $CF_3CF_2CH_2F$ (HFC-236cb). The conditions (particularly the catalyst) may be selected so as to favour the formation of one isomer in the resultant fluoroalkene, for example the Z-isomer.

If isomerising the E isomer of HFC-1225ye to the Z isomer, a preferred catalyst for use in the process of the invention is a Lewis acid catalyst (e.g. supported or preferably unsupported $SbF_5$) or a chromia-containing catalyst (e.g. a zinc/chromia catalyst).

The invention will now be illustrated, but not limited, by the following examples.

EXAMPLE 1

Liquid Phase Isomerisation of HFC-1225ye Using $SbF_5$ $SbF_5$ was charged to a 50 ml Hastalloy C reactor inside a nitrogen-purged glove box. The reactor was sealed inside the glove box, removed, placed in a heating block and pressure tested. An aliquot of a mixture of 87.8% E-HFC-1225ye and 9.1% Z—HFC-1225ye and the balance being a mixture of minor amounts of HFC-227ea, HFC-236ea, HFC-236cb and hexafluoropropene, was then added to the reactor and the contents stirred and heated. Vapour samples were periodically taken from the reactor to monitor the progress of the isomerisation. The experiment was repeated (experiment 1a) using the same catalyst as experiment 1. A further experiment (2) was also conducted using a higher catalyst loading at lower temperature. The results of experiments 1, 1a and 2 are summarized in Table 1 below.

TABLE 1

| | | | | | 1225ye isomeric composition (%) | |
|---|---|---|---|---|---|---|
| Experiment | $SbF_5$ (g) | 1225ye (g) | Temperature (° C.) | Time (min) | Z-1225ye | E-1225ye |
| 1 | 2.7 | 18.6 | 45 | 0 | 9.1 | 87.8 |
| | | | | 45 | 34.3 | 63.9 |
| | | | | 80 | 86.5 | 10.2 |
| | | | | 120 | 94.7 | 3.5 |
| | | | | 150 | 92.2 | 2.4 |
| | | | | 180 | 93.3 | 2.3 |
| | | | $SbF_5$ from Expt 1 re-used | | | |
| 1a | 2.7 | 21.4 | 45 | 0 | 9.1 | 87.8 |
| | | | | 70 | 42.2 | 54.8 |
| | | | | 100 | 79.2 | 18.1 |
| | | | | 170 | 87.1 | 10.0 |
| | | | | 200 | 90.6 | 6.7 |

TABLE 1-continued

| Experiment | SbF$_5$ (g) | 1225ye (g) | Temperature (° C.) | Time (min) | Z-1225ye | E-1225ye |
|---|---|---|---|---|---|---|
|  |  |  |  | 240 | 92.1 | 5.3 |
| Higher catalyst loading at lower temperature ||||||||
| 2 | 5.2 | 20.2 | 30 | 0 | 9.1 | 87.8 |
|  |  |  |  | 90 | 43.2 | 53.6 |
|  |  |  |  | 150 | 82.4 | 14.8 |
|  |  |  |  | 210 | 92.4 | 3.6 |

These experiments demonstrate that E-1225ye can be isomerised to Z-1225ye using SbF$_5$ under mild conditions. It appeared that any reduction in rate at lower temperature could be mitigated by increasing the catalyst loading.

EXAMPLE 2

Preparative Liquid Phase Isomerisation of HFC-1225ye Using SbF$_5$

The initial catalyst charge was prepared by dissolving SbF$_5$ in 87.8% E-HFC-1225ye, 9.1% Z—HFC-1225ye and the balance being a mixture of minor amounts of HFC-227ea, HFC-236ea, HFC-236cb and hexafluoropropene inside a nitrogen-purged glove box and transferring it under vacuum to a chilled 300 ml Inconnel reactor. The reactor was pressure tested and purged with nitrogen before charging and was equipped with a stirrer and band heater. Once charged, the mixture was stirred and allowed to warm to room temperature, if necessary heat was applied. As before, samples of vapour were periodically taken for analysis. At the end of each experiment the HFC-1225ye was recovered by distillation, leaving the catalyst in the reactor for re-use. A series of experiments was performed and these are summarized in Table 2 below.

TABLE 2

| Experiment | SbF$_5$ (g) | 1225ye (g) | Temperature (° C.) | Time (min) | Z-1225ye | E-1225ye | 236ea |
|---|---|---|---|---|---|---|---|
| 1 | 29.42 | 205 | 45 | 0 | 16.7 | 82.8 | — |
|  |  |  |  | 60 | 85 | 1.7 | 11.2 |
| Catalyst from expt 1 re-used |||||||||
| 1a | 29.42 | 163 | 30 | 0 | 18 | 81.8 | — |
|  |  |  |  | 40 | 64.2 | 33.1 | 0.46 |
|  |  |  |  | 60 | 76.8 | 21.3 | 0.62 |
|  |  |  |  | 90 | 83.5 | 14.4 | 0.75 |
|  |  |  |  | 120 | 88.4 | 9.4 | 0.86 |
|  |  |  |  | 140 | 89.2 | 6.7 | 0.76 |
|  |  |  |  | 220 | 93.3 | 4.6 | 1.1 |
| Catalyst from expt 1 and 1a re-used |||||||||
| 1b | 29.42 | 168 | 22 | 0 | 18 | 81.8 | — |
|  |  |  |  | 40 | 52.3 | 47.2 | 0 |
|  |  |  |  | 80 | 67.3 | 31.8 | 0.15 |
|  |  |  |  | 120 | 78.4 | 20.8 | 0.17 |
|  |  |  |  | 150 | 86 | 13.2 | 0.2 |
|  |  |  |  | 270 | 91.6 | 7.3 | 0.2 |
|  |  |  |  | 390 | 94.5 | 4.5 | 0.3 |
|  |  |  |  | 1080 | 97.4 | 1.8 | 0.34 |
| Catalyst from expt 1, 1a and 1b re-used |||||||||
| 1c | 29.42 | 188 | 21 | 0 | 18 | 81.8 | — |
|  |  |  |  | 90 | 48.4 | 50.7 | 0 |
|  |  |  |  | 120 | 68.7 | 30.5 | 0.04 |
|  |  |  |  | 200 | 74.7 | 24.6 | 0.05 |
|  |  |  |  | 1140 | 97.5 | 1.6 | 0.1 |
| Catalyst from expt 1, 1a, 1b and 1c re-used |||||||||
| 1d | 29.42 | 200 | 21 | 0 | 18 | 81.8 | — |
|  |  |  |  | 201 | 60.5 | 39.1 | 0 |
|  |  |  |  | 1080 | 83.2 | 16.4 | 0.09 |

The results show that Z-1225ye can be prepared from E-1225ye on a larger scale using SbF$_5$ under mild conditions. The formation of HFC-236ea (CF$_3$CFHCF$_2$H) implies that the initially potent SbF$_5$ is stripping some HF from the HFC-1225ye feed and the HFC-1225ye is then being hydrofluorinated by the HF. However, after the first run, much less HFC-236ea is formed and the process is more selective for isomerisation to Z-1225ye.

EXAMPLE 3a

Vapour Phase Isomerisation Over 6% Zn/Chromia in the Absence of HF

A 2 g sample of amorphous 6.0% Zn/chromia catalyst was charged to a 15 cm×1.25 cm Inconnel reactor tube. The catalyst was dried (250° C. for 1 hour) and pre-fluorinated (N$_2$:HF molar ratio of 6:1 for 1 hour at 250° C., temperature ramped to 380° C., nitrogen diluent switched off and left overnight). Following pre-fluorination the reactor was cooled. Then a mixture of 5 ml/min nitrogen and 1 ml/min of a mixture of 87.8% E-HFC-1225ye, 9.1% Z—HFC-1225ye, and the balance being a mixture of minor amounts of HFC-227ea, HFC-236ea, HFC-236cb and hexafluoropropene was passed over the catalyst and the effect of temperature on the isomerisation of E-1225ye to Z-1225ye explored. The results are presented in Table 3 below.

TABLE 3

| Temperature (° C.) | HFC-1225ye isomeric composition ||
|---|---|---|
|  | Z-1225ye | E-1225ye |
| 50 | 10.8 | 87.7 |
| 70 | 12.5 | 85.4 |
| 90 | 20.2 | 77.6 |
| 110 | 61.7 | 36.2 |
| 130 | 94.4 | 3.8 |

The data in Table 3 illustrates that the isomerisation can be effected over Zn/chromia based catalysts at modest temperatures in the absence of HF.

EXAMPLE 3b

Vapour Phase Isomerisation Over 6% Zn/Chromia in the Absence of HF Including Catalyst Regeneration In this experiment, the coking characteristics of the isomerisation process in the absence of HF were explored. The same conditions were used as for Example 3a but the temperature was maintained at 130° C. and the mixture of 87.8% E-HFC-1225ye, 9.1% Z—HFC-1225ye and the balance being a mixture of minor amounts of HFC-227ea, HFC-236ea, HFC-236cb and hexafluoropropene fed over the catalyst at 5 ml/min whilst monitoring the conversion of the E-isomer to the Z-isomer. After the conversion began to drop, the feed flow was stopped and the catalyst regenerated using a mixture of nitrogen (40 ml/min) and air (4 ml/min) at 380° C. for 12-16 hours. At the end of the regeneration the air feed was switched off and the catalyst was cooled to 130° C. When the catalyst had cooled the isomerisation cycle was repeated. The results of this isomerisation/regeneration/isomerisation cycle are presented in Table 4 below.

TABLE 4

| Time (mins) | 1225ye isomeric composition % | |
|---|---|---|
|  | Z-1225ye | E-1225ye |
| Cycle 1: | | |
| 8 | 91.4 | 3.8 |
| 43 | 94.4 | 3.8 |
| 63 | 94.6 | 3.7 |
| 93 | 94.5 | 3.7 |
| 119 | 94.5 | 3.9 |
| 155 | 94.6 | 3.9 |
| 181 | 92.0 | 3.7 |
| 213 | 93.1 | 4.0 |
| 298 | 89.1 | 9.5 |
| 335 | 85.7 | 12.6 |
| 358 | 79.7 | 19.2 |
| 378 | 76.5 | 22.0 |
| Cycle 2: | | |
| 10 | 95.0 | 3.7 |
| 35 | 94.4 | 3.7 |
| 70 | 94.6 | 3.8 |
| 95 | 94.4 | 3.8 |
| 125 | 94.6 | 3.8 |
| 150 | 94.7 | 3.9 |
| 185 | 94.3 | 4.1 |
| 215 | 94.0 | 4.7 |
| 241 | 91.7 | 7.0 |
| 270 | 86.0 | 12.5 |
| 300 | 75.0 | 23.4 |

These experiments demonstrated that:

The catalyst retained its isomerisation activity for a significant period in the absence of HF The isomerisation performance began to deteriorate after 4-5 hrs of contacting An air/nitrogen regeneration restored the catalyst to its original state, and therefore it can be concluded the loss of performance was due to coking-type reactions

EXAMPLE 4

Vapour Phase Isomerisation Over 6% Zn/Chromia in the Presence of HF

Example 3a was repeated using the original sample of catalyst except that 5 ml/min of HF was co-fed with the mixture of 87.8% E-HFC-1225ye, 9.1% Z—HFC-1225ye, and the balance being a mixture of minor amounts of HFC-227ea, HFC-236ea, HFC-236cb and hexafluoropropene over the catalyst. The results are shown in Table 5 below.

TABLE 5

| Temperature (° C.) | 1225ye isomeric composition | | |
|---|---|---|---|
|  | Z-1225ye | E-1225ye | 236ea |
| 130 | 6.4 | 92.3 | 0.0 |
| 130 | 6.4 | 92.0 | 0.0 |
| 150 | 6.6 | 92.0 | 0.0 |
| 170 | 7.6 | 91.0 | 0.0 |
| 190 | 8.0 | 90.4 | 0.0 |
| 210 | 8.9 | 89.0 | 0.0 |
| 230 | 16.7 | 81.5 | 0.1 |
| 250 | 61.3 | 36.7 | 0.3 |
| 270 | 85.4 | 9.8 | 2.9 |
| 290 | 75.6 | 9.8 | 12.5 |
| 310 | 70.9 | 9.6 | 16.6 |

Table 5 clearly shows that in the presence of HF much higher temperatures are required to effect a similar degree of isomeric conversion to that seen in the absence of HF. A temperature of 270° C. was found necessary, much higher than the 130° C. found necessary where HF was absent. Additionally, at high temperatures HF addition to the olefin was observed generating the saturated compound HFC-236ea.

EXAMPLE 5

Vapour Phase Isomerisation Over 6% Zn/Chromia with HF Including Catalyst Regeneration Example 3b was repeated except that the catalyst used in Example 4 was used in the first cycle (i.e. without prior regeneration). The results of the subsequent isomerisation/regeneration/isomerisation cycle are presented in Table 6 below.

TABLE 6

| | 1225ye isomeric composition | | |
|---|---|---|---|
| | Z-1225ye | E-1225ye | 236ea |
| Cycle 1: | | | |
| Time (mins) | | | |
| 390 | 83.4 | 9.7 | 4.6 |
| 400 | 87.8 | 9.9 | 1.5 |
| 430 | 86.5 | 9.7 | 2.9 |
| 485 | 85.5 | 9.7 | 3.8 |
| 515 | 86.5 | 9.2 | 3.4 |
| 545 | 85.7 | 9.5 | 3.6 |
| 575 | 86.8 | 9.2 | 3.4 |
| 605 | 86.0 | 9.7 | 3.6 |
| 665 | 87.0 | 9.5 | 2.6 |
| 725 | 87.2 | 9.6 | 2.4 |
| 780 | 87.0 | 10.1 | 1.5 |
| 810 | 68.5 | 30.5 | 0.1 |
| 880 | 72.0 | 27.0 | 0.1 |
| 940 | 70.5 | 27.7 | 0.0 |
| Cycle 2: | | | |
| Time (Hrs:mins) | | | |
| 0:15 | 85.7 | 9.8 | 0.9 |
| 0:45 | 84.5 | 9.2 | 3.8 |
| 1:30 | 82.4 | 9.8 | 4.7 |
| 2:15 | 84.9 | 9.3 | 4.4 |
| 3:15 | 86.2 | 9.9 | 2.9 |
| 04:00 | 85.9 | 9.2 | 3.8 |
| 04:45 | 86.1 | 9.0 | 4.0 |
| 05:00 | 87.1 | 9.7 | 2.3 |
| 05:45 | 82.6 | 9.0 | 5.7 |

TABLE 6-continued

<table>
<tr><th></th><th colspan="3">1225ye isomeric composition</th></tr>
<tr><th></th><th>Z-1225ye</th><th>E-1225ye</th><th>236ea</th></tr>
<tr><td>06:30</td><td>83.3</td><td>9.2</td><td>6.1</td></tr>
<tr><td>07:15</td><td>83.0</td><td>8.7</td><td>6.2</td></tr>
<tr><td>08:00</td><td>81.6</td><td>9.2</td><td>6.6</td></tr>
<tr><td>08:45</td><td>83.6</td><td>9.2</td><td>6.3</td></tr>
<tr><td>09:30</td><td>83.2</td><td>8.7</td><td>6.4</td></tr>
<tr><td>10:15</td><td>84.0</td><td>8.8</td><td>6.2</td></tr>
<tr><td>11:00</td><td>84.3</td><td>8.8</td><td>6.1</td></tr>
<tr><td>11:45</td><td>84.2</td><td>9.5</td><td>5.5</td></tr>
<tr><td>12:15</td><td>83.9</td><td>9.4</td><td>5.7</td></tr>
<tr><td>12:30</td><td>88.0</td><td>9.5</td><td>1.8</td></tr>
<tr><td>13:30</td><td>84.5</td><td>9.7</td><td>5.0</td></tr>
<tr><td>14:15</td><td>83.3</td><td>8.9</td><td>5.4</td></tr>
<tr><td>14:15</td><td>83.3</td><td>8.9</td><td>5.4</td></tr>
<tr><td>15:00</td><td>83.7</td><td>9.3</td><td>5.3</td></tr>
<tr><td>16:00</td><td>84.9</td><td>9.1</td><td>5.1</td></tr>
<tr><td>17:00</td><td>84.0</td><td>9.2</td><td>5.1</td></tr>
<tr><td>18:00</td><td>84.4</td><td>9.3</td><td>5.1</td></tr>
<tr><td>18:45</td><td>84.9</td><td>9.1</td><td>5.3</td></tr>
<tr><td>19:30</td><td>85.1</td><td>9.2</td><td>5.1</td></tr>
<tr><td>19:40</td><td>87.6</td><td>9.7</td><td>1.9</td></tr>
<tr><td>20:25</td><td>85.6</td><td>9.3</td><td>4.2</td></tr>
<tr><td>21:25</td><td>85.3</td><td>9.6</td><td>4.2</td></tr>
<tr><td>22:25</td><td>84.3</td><td>10.8</td><td>4.2</td></tr>
<tr><td>23:25</td><td>85.3</td><td>9.5</td><td>4.1</td></tr>
</table>

The data demonstrates that the catalyst retains its activity for longer when HF was co-fed even though the operating temperature was relatively high. The catalyst appeared to lose its hydrofluorination activity—as evidenced by the HFC-236ea levels—faster than it lost its isomerisation activity. As before, activity could be restored by an air/nitrogen regeneration. In cycle 2 the benefit of starting with a freshly regenerated catalyst was apparent with no deterioration in performance even after 24 hrs of contacting.

EXAMPLE 6

Isomerisation Over Pure Chromia Catalyst

The reactor tube was charged with 2 g of a pure chromia catalyst, which was dried at 250° C. under nitrogen (65 ml/min) for 2 hours. The catalyst was then pre-fluorinated with HF (30 ml/min) and nitrogen (65 ml/min) for 1 hour at 250° C. The temperature was then ramped to 460° C. and the pre-fluorination continued under neat HF (30 ml/min) overnight.

Mixed E/Z-1225ye (67:33, 5 ml/min), HF (6 ml/min) and purge nitrogen (1 ml/min) was then passed over the catalyst at temperatures between 100-360° C. in 20° C. steps. Two reactor off-gas samples were taken at each temperature. The results are summarized below:

| Temperature (° C.) | Z-1225ye (wt %) | E-1225ye (wt %) |
|---|---|---|
| 100 | 32.7 | 67.2 |
| 100 | 32.7 | 67.2 |
| 120 | 33.3 | 66.6 |
| 120 | 33.3 | 66.6 |
| 140 | 34.0 | 65.8 |
| 140 | 33.9 | 65.9 |
| 160 | 38.5 | 61.4 |
| 160 | 38.9 | 60.9 |
| 180 | 57.4 | 42.3 |
| 180 | 59.3 | 40.4 |
| 200 | 82.0 | 17.3 |
| 200 | 82.3 | 17.0 |
| 220 | 84.1 | 13.9 |
| 220 | 84.1 | 13.8 |
| 240 | 79.3 | 13.3 |
| 240 | 77.7 | 12.5 |
| 260 | 64.2 | 10.7 |
| 260 | 63.0 | 10.5 |
| 280 | 56.7 | 9.5 |
| 280 | 55.0 | 9.2 |
| 300 | 59.3 | 10.7 |
| 320 | 64.9 | 12.7 |
| 340 | 69.1 | 14.5 |
| 360 | 72.1 | 16.4 |

The invention claimed is:

1. A process for isomerising a (hydro)fluorobutene or (hydro)fluoropropene, the process comprising contacting the (hydro)fluorobutene or (hydro)fluoropropene with a catalyst which is a chromia-containing catalyst supported on $AlF_3$ or fluorinated alumina, wherein the chromia-containing catalyst contains an additional metal selected from zinc, magnesium, nickel, cobalt, silver, copper, aluminium, tin, zirconium, and mixtures thereof.

2. A process for isomerising a (hydro)fluorobutene or (hydro)fluoropropene, the process comprising contacting a E-(hydro)fluorobutene or E-(hydro)fluoropropene with a catalyst which is a chromia-containing catalyst supported on $AlF_3$ or fluorinated alumina to convert the E-(hydro)fluorobutene or E-(hydro)fluoropropene to a Z-(hydro)fluorobutene or Z-(hydro)fluoropropene, wherein the chromia-containing catalyst contains an additional metal selected from zinc, magnesium, nickel, cobalt, silver, copper, aluminium, tin, zirconium, and mixtures thereof.

3. A process according to claim 1, wherein the isomerisation results in the changing of the ratio of the E and Z isomers.

4. A process according to claim 3, wherein the ratio of the Z isomer to the E isomer increases.

5. A process according to claim 1, wherein the isomerisation is carried out as an in situ step in the synthesis of the (hydro)fluorobutene or (hydro)fluoropropene.

6. A process according to claim 5, wherein the isomerisation results in a changing of the ratio of the E to Z isomer compared to what it would have been if the catalyst had not been utilized.

7. A process according to claim 1, wherein the ratio of E to Z isomers changes from that which is the kinetic equilibrium from the reaction preparing the (hydro)fluorobutene or (hydro)fluoropropene.

8. A process according to claim 1, wherein the additional metal in the chromia-containing catalyst is present at a level of at least 0.01% by weight of the catalyst, or wherein the additional metal in the chromia-containing catalyst is present at a level of at least 0.1% by weight of the catalyst, or wherein the additional metal in the chromia-containing catalyst is present at a level of at least 1% by weight of the catalyst, or wherein the additional metal in the chromia-containing catalyst is present at a level of no more than 20% by weight of the catalyst, or wherein the additional metal in the chromia-containing catalyst is present at a level of no more than 10% by weight of the catalyst.

9. A process according to claim 1, wherein the (hydro)fluoropropene has the formula $CX_3CX=CX_2$ wherein each X is, independently, H or F provided that at least one X is F and at least one X is H, Cl, Br or I.

10. A process according to claim 9, wherein the (hydro)fluoropropene is selected from the monofluoropropene 1-fluoropropene (CH$_3$CH=CHF), the difluoropropenes 1,2-difluoropropene (HFC=CFCH$_3$) and 1,3-difluoropropene (HFC=CHCH$_2$F), the trifluoropropenes 1,2,3-trifluoropropene (HFC=CFCH$_2$F) and 1,3,3-trifluoropropene (HFC=CHCF$_2$H), the tetrafluoropropenes 1,3,3,3-tetrafluoropropene (HFC=CHCF$_3$) and 1,2,3,3-tetrafluoropropene (HFC=CFCF$_2$H), and the pentafluoropropene 1,2,3,3,3-pentafluoropropene (HFC=CFCF$_3$).

11. A process according to claim 1 conducted at a temperature of from −50 to 400° C., and/or a pressure of from 0 to 30 bara, and/or conducted in the presence of HF.

* * * * *

UNITED STATES PATENT AND TRADEMARK OFFICE
CERTIFICATE OF CORRECTION

PATENT NO. : 8,742,181 B2
APPLICATION NO. : 13/683893
DATED : June 3, 2014
INVENTOR(S) : Andrew Paul Sharratt and John Charles McCarthy Page 1 of 1

It is certified that error appears in the above-identified patent and that said Letters Patent is hereby corrected as shown below:

Title page, item (57) Abstract
in line 3 of the abstract, after "a catalyst" delete "a catalyst"

Signed and Sealed this
Seventeenth Day of March, 2015

Michelle K. Lee
*Director of the United States Patent and Trademark Office*